United States Patent [19]

Lipinski

[11] Patent Number: 4,575,507

[45] Date of Patent: Mar. 11, 1986

[54] SPIRO-IMIDAZOLIDINES AS ALDOSE REDUCTASE INHIBITORS AND THEIR PHARMACEUTICAL USE

[75] Inventor: Christopher A. Lipinski, Waterford, Conn.

[73] Assignee: Pfizer Inc., New York, N.Y.

[21] Appl. No.: 738,924

[22] Filed: May 29, 1985

[51] Int. Cl.[4] ............... A61K 31/415; C07D 471/10; C07D 491/07; C07D 233/78
[52] U.S. Cl. .................. 514/278; 514/389; 546/18; 548/308; 548/309
[58] Field of Search ............ 546/18; 548/308, 309; 514/278, 389

[56] References Cited

U.S. PATENT DOCUMENTS 4,235,911 11/1980 Sarges .................. 346/18
4,540,704 9/1985 Ueda et al. .............. 548/309

*Primary Examiner*—Robert T. Bond
*Attorney, Agent, or Firm*—Charles J. Knuth; Albert E. Frost; James M. McManus

[57] ABSTRACT

Compounds related to 3',4'-dihydrospiro[imidazolidine-4,1'(2'H)-naphthalene]2,3',5-trione, spiro[chroman-4,4'-imidazolidine]2,2',5'-trione and 1',2'-dihydrospiro[imidazolidine-4,4'-(3'H)-quinoline 2,2'5-trione and reduced products thereof as aldose reductase inhibitors.

11 Claims, No Drawings

SPIRO-IMIDAZOLIDINES AS ALDOSE REDUCTASE INHIBITORS AND THEIR PHARMACEUTICAL USE

BACKGROUND OF THE INVENTION

This invention relates to novel spiroimidazolidines useful in the treatment of certain chronic complications arising from diabetes mellitus, such as diabetic cataracts, retinopathy and neuropathy, to pharmaceutical compositions containing such compounds and to a method of using these compounds.

In the past various attempts have been made to obtain more effective oral anti-diabetic agents. Generally these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]isoquinoline-2(3H)-acetic acid and derivatives thereof to be useful for the treatment of these conditions. U.S. Pat. No. 4,117,230 teaches the use of certain hydantoins for treating complications of diabetes as aldose reductase inhibitors. Such aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way unwanted accumulations of galactitol in the lens of galactosemic subjects and of sorbitol in the lens, of peripheral nervous cord and kidneys of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

Beta-carbonyl analogs of the instantly claimed compounds are disclosed in my pending U.S. application Ser. No. 545,450, filed Oct. 28, 1983.

SUMMARY OF THE INVENTION

The compounds of the present invention are spiroimidazolidines of the formula:

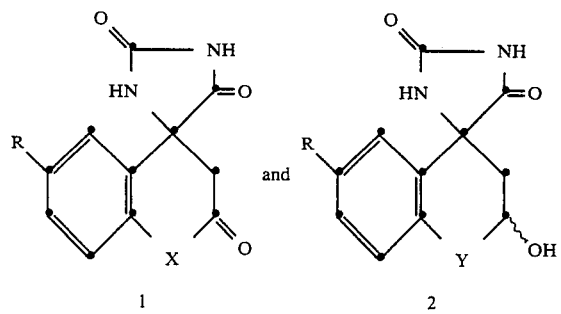

and the pharmaceutically acceptable salts thereof, wherein X is O, CH$_2$ or NH; R is hydrogen, fluoro, chloro, methyl or methoxy; and Y is O or CH$_2$.

A preferred group of compounds related to 1 are those wherein X is CH$_2$. Especially preferred within this group are those compounds wherein R is hydrogen or fluoro.

Also preferred are compounds related to 1 where X is NH. Especially preferred is the compound where R is chloro.

A preferred group of compounds related to 2 are those where Y is O. Especially preferred is the compound where R is fluoro.

Also included as part of the present invention are pharmaceutical compositions comprising a pharmaceutically-acceptable carrier and a compound selected from formula 1 or 2, wherein the weight ratio of the pharmaceutically acceptable carrier to said compound is in the range of 1:4 to 20:1.

The present invention further comprises a method of treating a diabetic host to prevent or alleviate ocular or neuritic diabetes-associated chronic complications, which comprises administering to said diabetic host an alleviating or prophylactically effective amount of a compound selected from those of formula 1 or 2.

DETAILED DESCRIPTION

The spiro compounds of formula 1 wherein X is CH$_2$, have the following numbering system:

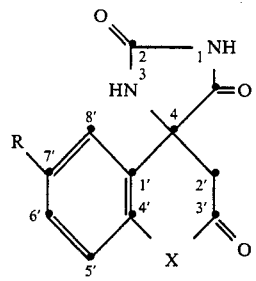

They are prepared according to the following reaction steps:

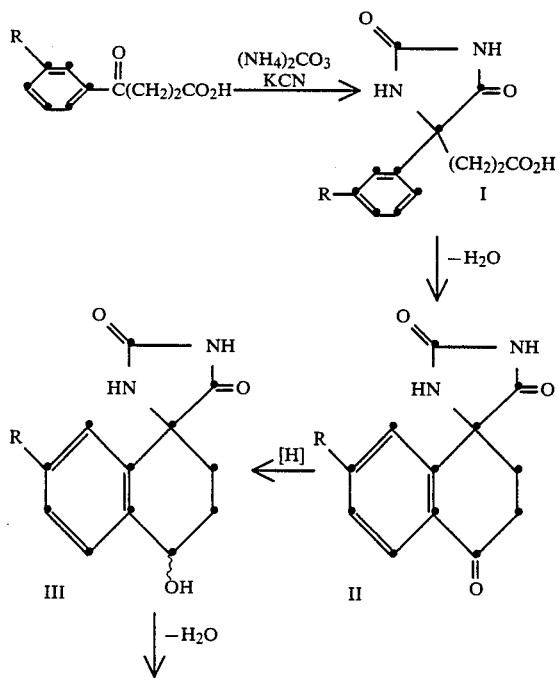

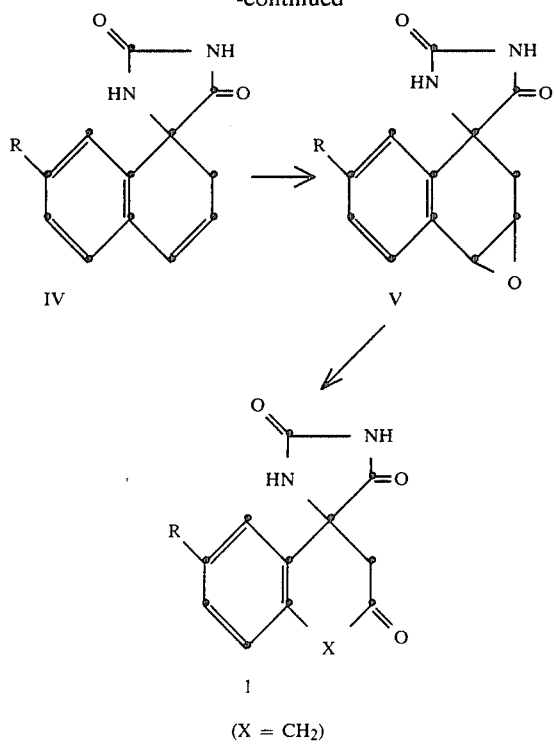

(X = CH₂)

In the initial step, treatment of one mole of the appropriate m-substituted benzoylpropionic acid with ten moles of ammonium carbonate and two moles of potassium cyanide in an aqueous medium at 70° C. for about 24 hours results in the formation of the desired imidazolidine intermediate I.

Compound I is cyclized to II by treatment with concentrated sulfuric acid at 100° C. for 1–2 hours.

Reduction of the carbonyl function of II with a molar excess of sodium borohydride provides a mixture of isomeric alcohols, III.

The alcohols, III, are subsequently dehydrated on treatment with -toluenesulfonic acid in refluxing toluene, giving rise to the corresponding dihydronaphthalenes, IV.

Epoxidation of IV with m-chloroperbenzoic acid results in the formation of epoxide V.

Finally, treatment of V with about two equivalents of boron trifluoride etherate in a reaction-inert solvent results in the formation of the final product, 1(X=CH₂).

The reaction is preferably carried out in the cold, usually at about 0° C. Higher temperatures may shorten the reaction time, but also leads to unwanted by-products. At the preferred reaction temperature product formation is complete in about one hour.

The preferred reaction solvent is tetrahydrofuran, although any solvent which does not react with starting reagents or product and solubilizes the reactants at the reaction temperature can be employed.

On completion, the reaction mixture is quenched with water, and the product extracted with a water-immiscible solvent such as toluene, methylene chloride or ethyl acetate.

Purification of the product can be achieved by conventional means, such as recrystallization or chromatographing.

The benzoylpropionic acids employed as starting reagents for this synthetic route can be prepared by the procedures of Stelter, et al., *Chem. Ber.*, 107, 210 (1974), McEvoy, et al., *J. Org. Chem.*, 38, 4044 (1973) or Fieser, et al., *J. Am. Chem. Soc.*, 58, 2314 (1936).

Spiro compounds of formula 1 wherein X is —O— have the following numbering system:

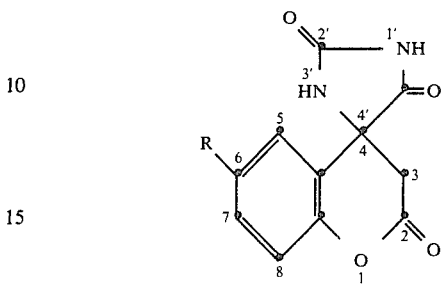

They are prepared by the following sequence of reactions:

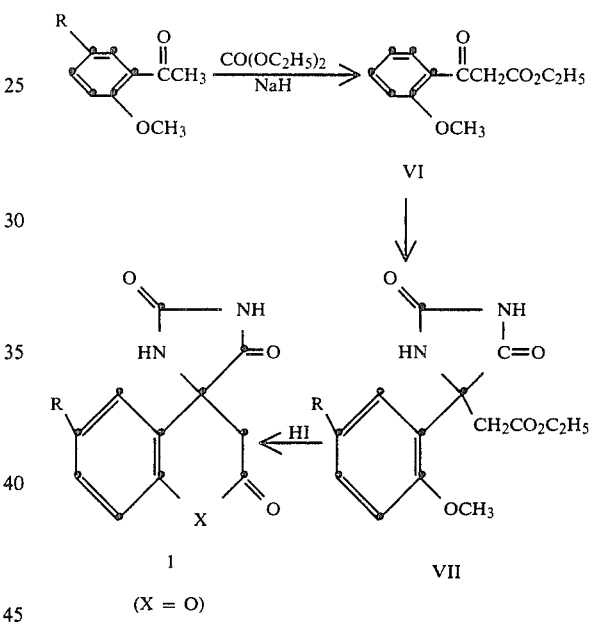

(X = O)

In the initial step, one mole of a O-methoxyacetophenone is condensed with diethyl carbonate in the presence of a base such as sodium hydride to give the corresponding benzoylacetate, VI.

Reaction of VI with ammonium carbonate and potassium cyanide results in the formation of the substituted imidazolidine 2,5-dione, VII.

Treatment of VII with an excess of hydriodic acid results in hydrolysis of the O-methoxy group and cyclization to 1 (X=O). This reaction is conducted at elevated temperatures, with a preferred temperature of about 100° C. Lower temperature can be employed with corresponding longer reaction times. When the preferred reaction temperature is employed the reaction is substantially complete in about 6–8 hours.

On completion, the reaction mixture is diluted with water and the product filtered. Purification can be carried out by chromatographing or recrystallization.

The starting acetophenones can be prepared according to known procedures, such as those taught by Groggins, "Unit Processes in Organic Chemistry", McGraw-Hill Book Co., New York, 1947, p. 759-770.

Spiro compounds of formula 1 wherein X is NH have the following numbering system:

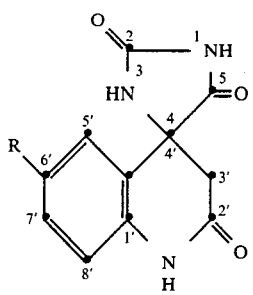

These spiro compounds are prepared by the following series of reactions:

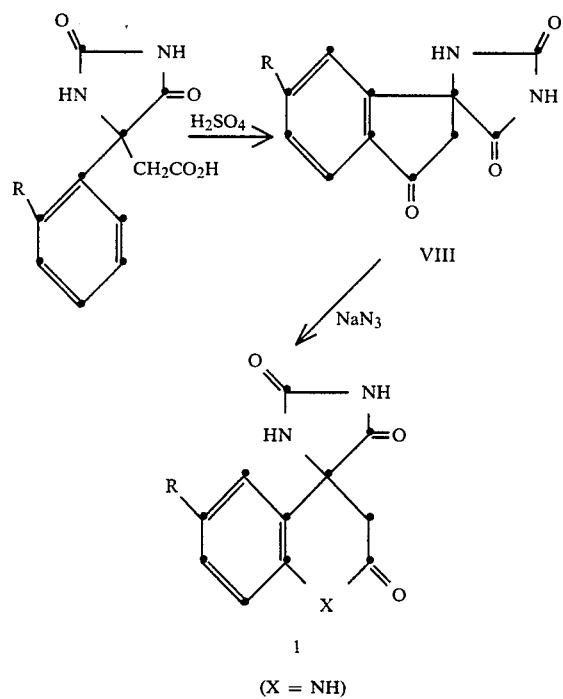

Treatment of the requisite 4-phenyl-4-(carboxymethyl)imidazolidine 2,5-dione with sulfuric acid at elevated temperatures results in cyclization to VIII.

Treatment of VIII with an equimolar amount of sodium azide in an excess of concentrated sulfuric acid at room temperature gives, after a reaction time of about 20-30 minutes, the desired product 1, (X=NH).

The starting 4-phenyl-4-(carboxymethyl)imidazolidine 2,5-diones can be prepared from the corresponding benzoylacetic acids by treatment with ammonium carbonate and an alkali metal cyanide such as potassium or sodium cyanide in water or an alcoholwater solution at a pH of about 9 to 10 and at a reaction temperature of 50°-100° C.

The compounds of formula 2 (Y=O or $CH_2$) are prepared by reduction of the corresponding carbonyl bearing compound using an aluminum hydride reducing agent, preferably diisobutylaluminum hydride. In practice, the corresponding carbonyl compound is reacted with an excess of the reducing agent in a reaction-inert solvent such as tetrahydrofuran at a reaction temperature of $-78°$ to $-40°$ C. On completion of the reaction, requiring about 30-60 minutes, the reaction mixture is added to 10% hydrochloric acid and the product, which consists of a mixture of epimeric alcohols, is filtered or extracted with a water-immiscible solvent such as ethyl acetate. Purification is by recrystallization or chromatographing.

Because of the acidic hydrogen atom in the spiroheterocyclic ring of the compounds of formulae 1 and 2 salts may be formed with pharmaceutically acceptable cations by conventional methods. Thus, these salts may be readily prepared by treating the compound of formulae, 1 or 2 with an aqueous solution of the desired pharmaceutically acceptable cation and evaporating the resulting solution to dryness, preferably under reduced pressure. Alternatively, a lower alkyl alcohol solution of the compound of formulae 1 or 2 may be mixed with an alkoxide of the desired metal and subsequently evaporating the solution to dryness. Suitable pharmaceutically acceptable cations for this purpose include, but are not limited to, alkali earth metal cations such as potassium and sodium, ammonium or water-soluble amine addition salts such as the lower alkanolammonium and other base salts with organic amines which are pharmaceutically acceptable and alkaline earth metal cations such as calcium and magnesium.

It is to be understood that by use of the term pharmaceutically acceptable salts in the disclosure and claims hereof it is meant to embrace both the acid addition salts and the salts formed with appropriate cations, as described above.

The novel compounds of formulae 1 and 2 and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention and alleviation of such conditions. The compound may be administered to a subject in need of treatment by a variety of conventional routes of administration, including orally, parenterally and topically. In general, these compounds will be administered orally or parenterally at dosages between about 0.05 and 25 mg./kg. body weight of the subject to be treated per day, preferably from about 0.1 to 10 mg./kg. However, some variation in dosage will necessarily occur depending on the condition of the subject being treated. The person responsible for administration will, in any event, determine the appropriate dose for the individual subject.

The novel compound of the invention may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the novel compounds of formula 1 or 2 and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula 1 or 2 sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Compounds of formulae 1 and 2 may not only be advantageously employed for the preparation of aqueous pharmaceutical compositions for parenteral administration, as described above, but more particularly for the preparation of pharmaceutical compositions suitable for use as ophthalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts the compounds of this invention are administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.). The ophthalmic preparation will contain a compound of formula 1 or 2 or a pharmaceutically acceptable salt thereof in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potassium borate, sodium and potassium carbonate, sodium acetate, sodium biphosphate and the like, in amounts sufficient to maintain the pH at between about 6 and 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve and lens of acutely streptozotocinized, i.e. diabetic, rats; (3) measuring their ability to reverse already-elevated sorbitol levels in the sciatic nerve and lens of chronic streptozotocin-induced diabetic rats; (4) measuring their ability to prevent or inhibit galacticol formation in the lens of acutely galactosemic rats; (5) measuring their ability to delay cataract formation and reduce the severity of lens opacities in chronic galactosemic rats; (6) measuring their ability to prevent sorbitol accumulation and cataract formation in isolated rat lens incubated with glucose; and (7) measuring their ability to reduce already elevated sorbitol levels in isolated rat lens incubated with glucose.

The present invention is illustrated by the following examples. It will be understood, however, that the invention is not limited to the specific details of these examples. Proton nuclear magnetic resonance spectra (NMR) were measured at 60 MHz (unless otherwise indicated) for solutions in perdeuterodimethyl sulfoxide (DMSO-$d_6$) and peak positions are expressed in parts per million (ppm) downfield from tetramethylsilane. The peak shapes are denoted as follows: s, singlet; d, doublet; t, triplet; q, quartet; m, multiplet; b, broad.

EXAMPLE 1

3', 4' Dihydro-7'-fluorospiro[imidazolidine-4,1'-(2'H)-napthalene]2,3',5-trione

A. 4-(m-fluorophenyl)-4-(carboxymethyl)imidazolidine 2,5-dione

To 60 ml. of water was added 1.57 g. (8m mole) of 3-(m-fluorobenzoyl)propionic acid (*Eur. J. Med. Chem.,* 13, 533 (1978), 7.7 g. (80 m mole) of ammomium carbonate and 1.04 g (16 m mole) of potassium cyanide, and the mixture heated to 70° C. for 20 hours. The reaction was cooled and the pH adjusted to 2 with 12N hydrochloric acid. The resulting precipitate was filtered and dried in vacuo, 1.8 g. (85% yield), m.p. 206°–208° C.

B. 3',4'-dihydro-7'-fluorospiro[imidazolidine-4-1'(2'H)-naphthalene]2,4',5-trione 4-(m-fluorophenyl)-4-(carboxymethyl)imidazolidine 2,5-dione (1.06 g., 4m mol) was added to 10 ml. of concentrated sulfuric acid and heated at 100° C. for 1.5 hours. The reaction was cooled in an ice bath and ice cautiously added to the reaction mixture. The resulting precipitate was filtered and recrystallized from water, 245 mg. (25% yield), m.p. 218°–220° C.

C. 3',4'-dihydro-4'-hydroxy-7'-fluorospiro[imidazolidine-4,1'(2'H)-naphthalene]2,5-dione To a solution of 15.5 g. (0.0625 mole) of 3',4'-dihydro-7'-fluorospiro [imidazolidine-4,1'(2'H)-naphthalene]2,4',5-trione in 300 ml. of methanol cooled to 0° C. was added 4.8 g. (0.012 mole) of sodium borohydride over a period of 20 minutes. After stirring for one hour at 0° C. 100 ml. of 10% hydrochloric acid was added and the methanol removed under vacuum. The solid suspension was filtered and the solids dried, 7.3 g. (47% yield).

D. 7'-fluorospiro[imidazolidine-4,1'(2'H)-naphthalene]2,5-dione

3',4',-Dihydro-4'-hydroxy-7'-fluorospiro[imidazolidine-4,1'(2'H)-naphthalene]2,5-dione (3.2 g., 0.013 mole) was added to 75 ml. of toluene containing a trace of -toluenesulfonic acid and the mixture heated to reflux for 5 hours. The toluene was removed in vacuo and the residue triturated with diethyl ether and filtered, 2.6 g. (87% yield).

E. 3',4'-Dihydro-3',4'-epoxy-7'-fluorospiro[imidazolidine-4,1'(2'H)-naphthalene]2,5-dione To a slurry of 2.6 g. (0.011 mole) of 7'-fluorospiro[imidazolidine-4,1'(2'H)-naphthalene]2,5-dione in 50 ml. of chloroform was added 125 ml. of a 5% sodium bicarbonate solution followed by 3.0 g. (0.014 mole) of m-chloroperbenzoic acid. The reaction mixture was allowed to stir at room temperature for 4 hours after which an additional 1.2 g. (0.0055 mole) of m-chloroperbenzoic acid were added. After stirring overnight at room temperature the mixture was poured into 100 ml. of a 5% sodium bicarbonate solution and the mixture extracted (2×100 ml.) with chloroform and then with ethyl acetate (2×100 ml.). The organic extracts were combined, washed with water and a brine solution and dried over magnesium sulfate. Removal of the solvent gave 600 mg. (22% yield) of the desired product.

F. 3',4'-Dihydro-7'-fluorospiro[imidazolidine-4,1'-(2'H)-naphthalene]2,3',5-trione To a suspension of 600 mg. (0.0024 mole) of 3',4'-dihydro-3',4'-epoxy-7'-fluorospiro [imidazolidine4,1'(2'H)-naphthalene]2,5-dione in 50 ml. of tetrahydrofuran at 0° C. and under a nitrogen atmosphere was added 0.6 ml. (0.0048 mole) of boron trifluoride etherate, and the reaction mixture allowed to stir at 0° C. for one hour. Water (50 ml.) was added and the reaction product extracted with ethyl acetate (3×50 ml.). The combined extracts were washed with water and a brine solution, dried over magnesium sulfate and concentrated to a simi-solid. The product was purified by column chromatography using ethyl acetate-hexane (60:40; V:V) as the eluent, 220 mg. (36% yield), m.p. 289°–291° C. (dec.).

Anal. Calc'd for $C_{12}H_9O_3N_2F$: C, 58.1; H, 3.7; N, 11.3. Found: C, 57.5; H, 3.6; N, 11.1.

In a similar manner, starting with 3-(m-chlorobenzoyl)propionic acid and following the procedures of Example 1-A through 1-F, 3',4'-dihydro-7'-chlorospiro[imidazolidine-4',1')2'H)-naphthalene]2,3',5-trione is prepared.

Example 2

3',4'-Dihydrospiro[imidazolidine-4,1'(2'H)-naphthaline]2,3'-5-trione

A. 3',4'-Dihydrospiro[imidazolidine-4,1'(2'H)-naphthaline]2,3'-5-trione

A solution of 2.48 g. (10 m mole) of 4-phenyl-4-(carboxymethyl)imidazolidine 2,5 dione (C.A. reg. No. 30741-72-1) in 25 ml. of concentrated sulfuric acid was warmed at 90° C. for one hour and 120° C. for 45 minutes, and then poured on to ice. The resulting solid was filtered and dried, 1.85 g., m.p. 144°–149° C. Recrystallization from isopropanol gave 1.11 g. of desired product, m.p. 261°–263° C.

Anal. Calc'd. for $C_{12}H_{10}N_2O_3$: C, 62.6; H, 4.4; N, 12.2 Found: C, 62.3; H, 4.5; N, 12.2.

B. 3',4'-dihydro-4'-hydroxyspiro[imidazolidine 4,1'(2'H)-naphthalene]2,5-dione To a slurry of 14.3 g. (0.062 mole) of 3',4'-dihydrospiro[imidazolidine-4,1'(2'H)-naphthalene]2,4',5-trione in 250 ml. of methanol at 0° C. was added in small portions over a period of 15 minutes 4.8 g. (0.13 mole) of sodium borohydride, and the reaction mixture allowed to stir in the cold for 60 minutes. The reaction mixture was added to 250 ml. of 10% hydrochloric acid and 50 ml. of a brine solution. The product was extracted with ethyl acetate (5×50 ml.) and the extracts combined and washed with a 10% hydrochloric acid solution. The extracts were dried over magnesium sulfate and concentrated to give an off-white solid. Triturations with diethyl ether followed by filtration gave 4.5 g. (31.9% yield).

C. Spiro[imidazolidine-4,1'(2'H)-naphthalene]2,5-dione

To a refluxing solution of 100 ml. of toluene containing 4.5 g. (0.019 mole) of 3',4'-dihydro-4'-hydroxyspiro [imidazolidine-4,1'(2'H)-naphthalene]2,-5-dione was added a trace of -toluenesulfonic acid and the refluxing continued for 2 hours. The reaction was cooled, stripped to dryness and the residue dissolved in 100 ml. of ethyl acetate. The organic phase was washed with a saturated sodium bicarbonate solution, dried over sodium sulfate and concentrated to dryness. The residue was triturated with diethyl ether, 2.7 g. (65% yield).

D. 3',4'-dihydro-3',4'-epoxyspiro[imidazolidine-4,1'(2'H)-naphthalene]2,5-dione To a slurry of 2.7 g. (0.013 mole) of spiro[imidazolidine-4,1'(2'H)-naphthalene]-2,5-dione in 50 ml. of chloroform and 125 ml. of a 5% sodium bicarbonate solution was added 3.4 g. (0.016 mole) of m-chloroperbenzoic acid and the reaction mixture allowed to stir at room temperature for 3 hours. The reaction mixture was poured into 100 ml. of a 5% sodium bicarbonate solution and the product extracted with chloroform (2×75 ml.) and ethylacetate (2×75 ml.). The combined extracts were washed with a sodium bicarbonate solution and a brine solution, dried over sodium sulfate and concentrated to a yellow solid. Trituration with diethyl ether gave 1.6 g. (55% yield) of the desired product.

E.
3',4'-dihydrospiro[imidazolidine-4,1'(2'H)-naphthalene]2,3',5-trione

To a slurry of 1.0 g. (0.0044 mole) of 3',4'-dihydro-3'4'-epoxyspiro[imidazolidine-4,1'(2'H)-naphthalene]2,5-dione in 60 ml. of cold tetrahydrofuran and under an atmosphere of nitrogen was added 0.5 ml. of boron trifluoride/etherate, and the reaction mixture allowed to stir at 0° C. for 30 minutes. The solution was poured into 60 ml. of water and extracted with ethyl acetate (4×50 ml.). The combined extracts were washed with a sodium bicarbonate solution, water and a brine solution. The dried organic extracts were concentrated to an oil, which when triturated with diethyl ether gave 200 mg. of product (20% yield), m.p. 226°–227° C. (dec.).

Anal. Calc'd. for $C_{12}H_{10}O_3N_2$: C, 62.6; H, 4.3; N, 12.2. Found: C, 61.4; H, 4.6; N, 11.4.

The NMR spectrum ($D_6DMSO$) showed absorption at 10.98 (bs, 1H), 8.66 (s, 1H), 7.43–7.25 (m, 4H), 3.79 (AB, q, 2H, J=27, 18), 2.9 (AB, q, 2H, J=14.27)ppm.

Starting with 4-(m-methylphenyl)-4-(carboxymethyl)imidazolidine 2,5-dione and 4-(m-methoxyphenyl)-4-(carboxymethyl) imidazolidine 2,5-dione and following the procedures of Example 2H-2E, 3',4'-dihydro-7'-methylspiro[imidazolidine-4,1'(2'H)-naphthalene]2,3',5-trione and 3',4'-dihydro-7'-methoxyspiro[imidazolidine-4,1'(2'H)-naphthalene]2,3',5-trione are prepared, respectively.

EXAMPLE 3

Spiro[chroman-4,4'-imidazolidine]2,2',5'-trione

A. Ethyl O-methoxybenzoylacetate

To a suspension of 7.7 g. (0.32 mole of oil-free sodium hydride in 200 ml. of cold (0° C.) tetrahydrofuran containing 72.6 g. (0.61 mole) of diethyl carbonate was added dropwise under a nitrogen atmosphere 44 g. (0.29 mole) of O-methoxyacetophenone in 200 ml. of tetrahydrofuran. When the addition was complete, the reaction was allowed to stir at 0° C. for 2 hours. The reaction was cooled, poured into a 10% hydrochloric acid solution and extracted with ether. The combined extracts were washed with brine and water, dried over magnesium sulfate and concentrated in vacuo, 36 g.

B.
4-(O-methoxyphenyl)-4-(carbethoxymethyl)imidazolidine 2,5-dione

A mixture of 36 g. (0.16 mole) of ethyl O-methoxybenzoylacetate, 21 g. (0.32 mole) of potassium cyanide and 65 g. (0.67 mole) of ammonium carbonate in 700 ml. of 30% aqueous ethanol was heated at 60° C. for 5 days. The reaction mixture was cooled and carefully acidified with 12N hydrochloric acid. The ethanol was removed in vacuo and the resulting solids were filtered, washed with water, methanol and diethyl ether and dried to give 11 g. of the desired product.

C. Spiro[chroman-4,4'-imidazolidine]2,2',5'-trione 4-(O-Methoxyphenyl)-4-(carboethoxymethyl)imidazolidine 2,5-dione (5.0 g., 0.017 mole) was added to 30 ml. of 57% hydriodic acid and heated at 100° C. for 7 hours. The reaction mixture was cooled and poured into water. The solids were filtered, washed with water and dried. Recrystallization from methanol gave 1.3 g. of the desired product, m.p. 273°–276° C. (dec.).

Anal. Calc'd. for $C_{11}H_8O_4N_2$: C, 56.9; H, 3.5; N, 12.1. Found: C, 56.2; H, 3.7; N, 11.8.

The NMR spectrum ($D_6DMSO$) showed absorption at 11.1 (bs, 1H), 8.7 (s, 1H), 7.51–7.17 (m, 4H) and 3.26 (AB, q, 2H, J=16 and 14)ppm.

In a similar manner, starting with 2-methoxy-5-methylacetophenone and following the procedures of Example 3A-3C, 6-methylspiro[chroman-4,4'-imidazolidine]2,2',5'-trione is prepared.

EXAMPLE 4

6-Fluorospiro[chroman-4,4'-imidazolidine]2,2',5'-trione

A. Ethyl 2-methoxy-5-fluorobenzoylacetate

To a slurry of 4.35 g. (0.18 mole) of oil-free sodium hydride in 100 ml. of cold tetrahydrofuran under a nitrogen atmosphere was added 40 g. (0.34 mole) of diethyl carbonate followed by the dropwise addition of (0.18 mole) of 2-methoxy-5-fluoroacetophenone in 150 ml. of the same solvent. The reaction mixture was allowed to stir for one hour and was then heated to 60° C. for 4 hours. It was then cooled, poured into 10% hydrochloric acid and extracted with diethyl ether. The organic extracts were combined and the product extracted into 1N potassium hydroxide solution. The basic phase was separated, acidified with 12N hydrochloric acid and extracted with ether. The extracts were washed with water and a sodium bicarbonate solution, dried over magnesium sulfate and concentrated to an oil, 16.3 g. (38% yield).

B.
4-(2'-methoxy-5'-fluorophenyl)-4-(carboethoxymethyl)imidazolidine 2,5-dione

In a manner similar to Example 3B, 16.3 g. (0.068 mole) of ethyl 2-methoxy-5-fluorobenzaylacetate, 8.8 g. (0.136 mole) of potassium cyanide and 26.1 g. (0.272 mole) of ammonium carbonate in 350 ml. of aqueous ethanol gave after heating at 60° C. for 4 days, 4.0 g. (20% yield) of the desired product.

C.
6-fluorospiro[chroman-4,4'-imidazolidine]2,2',5'-trione

Starting with 4.0 g. (0.23 mole) of 4-(2'-methoxy-5'-fluorophenyl-4-(carboethoxymethyl) imidazolidine 2,5-dione and 50 ml. of 58% hydriodic acid and employing the procedure of Example 3C, 1.7 g. (53% yield) of the desired product was obtained, m.p. 298°–300° C. (dec.).

Anal. Calc'd. for $C_{11}H_7O_4N_2F$: C, 52.8; H, 3.0; N, 11.2. Found: C, 52.4; H, 2.8; N, 11.0.

The NHR spectrum ($D_6DMSO$) showed absorption at 11.15 (bs, 1H), 8.7 (s, 1H), 7.38–7.24 (m, 2H), 7.17 (d, d, 1H, J=3 and 10) and 3.28 (AB, q, 2H, J=16 and 15)ppm.

EXAMPLE 5

6-Chlorospiro[chroman-4,4'-imidazolidine]2,2',5'-trione

A. Ethyl 2-methoxy-5-chlorobenzaylacetate

In a manner similar to Examples 3A and 4A, 25.5 g. (0.14 mole) of 2-methoxy-5-chloroacetophenone, 6.7 g. (0.14 of sodium hydride and 33 g. (0.28 mole) of diethyl carbonate gave, on work up, 12.5 g. (35% yield) of the desired product as a yellow oil.

B.
4-(2'-methoxy-5'-chlorophenyl)-4-(carbethoxymethyl)imidazolidine 2,5-dione

Starting with 12.5 g (0.049 mole) of ethyl 2-methoxy-5-chlorobenzoylacetate, 6.3 g. (0.095 mole) of potassium cyamide and 18.7 g. (0.193 mole) of ammonium carbonate and following the procedure of Example 4B, there was obtained 4.0 g. (25% yield) of the desired product as a tan solid.

C.
6-chlorospiro[chroman-4,4'-imidazolidine]2,2',5'-trione

A solution of 4.0 g. (0.0122 mole) of 4-(2'-methoxy-5'-chlorophenyl)-4-(carboethoxymethyl)imidazolidine 2,5-dione in 40 ml. of 58% hydriodic acid was heated to 115° C. for 4 hours. The reaction mixture was cooled, poured into water and extracted with ethyl acetate. The combined extracts were washed with a sodium bisulfite solution, water and brine, dried over magnesium sulfate and concentrated in vacuo to dryness. The residue was chromatographed using ethyl acetatehexane as the eluent (1:1; V:V) to give 106 mg. of product as the less polar material, m.p. 289°–290° C. (dec.).

The NMR spectrum ($D_6$DMSO) showed absorptum at 11.19 (bs, 1H), 8.7 (s, 1H), 7.54 (d, d, 1H, J=2 and 8), 7.34 (d, 1H, J=2), 7.27 (d, 1H, J=8) and 3.3 (AB, 2H, J=16 and 14)ppm.

EXAMPLE 6

1',2'-Dihydrospiro[imidazolidine-4,4'(3'H)-quinoline]2,2',5-trione

A. Spiro[imidazolidine-4,1'(2'H)-indene]5 2,3',5-trione

A solution of 13.5 g. (0.058 mole) of 4-phenyl-4-(carboxymethyl)imidazolidine 2,5-dione in 50 ml. of concentrated sulfuric acid was heated to 120° C. for 5 hours. The reaction mixture was cooled, poured on to ice and extracted with ethyl acetate. The combined extracts were washed with water and brine, dried over magnesium and concentrated to dryness. The residue was triturated with diethyl ether-hexane (1:1) and the solids filtered and dried.

B.
1',2'-dihydrospiro[imidazolidine-4-4'(3'H)-quinoline]2',2,5-trione

A solution of 2.09 g. (0.0046 mole) of spiro [imidazolidine-4,1'(2'H)-indene]2,3',5-trione in 30 ml. of concentrated sulfuric acid was treated portion-wise with 300 mg. (0.0046 mole) of sodium azide. After completion of the addition the reaction was allowed to stir at room termperature for 20 minutes, was poured into ice water and extracted with ethyl acetate. The extracts were combined, washed with water, and saturated sodium bicarbonate solution and brine and dried over magnesium sulfate. Removal of the solvent under vacuum gave the product as a yellow solid. The product was recrystallized from ethanol, m.p. 257°–260° C.(dec.).

The NMR spectrum ($D_6$ DMSO) showed absorption at 10.95 (bs, 1H), 10.33 (s, 1H), 8.55 (s, 1H), 7.32 (t, 1H, J=8), 7.15 (d, 1H, J=8), 7.05 (d, 1H, J=8), 6.98 (t, 1H, J=8) and 2.85 (AB, q, 2H, J=16 and 14)ppm.

In a similar manner, starting with 4-(3'-fluorophenyl)-4-(carboxymethyl) imidazolidine 2,5-dione, 4-(3'-tolyl)-4-(carboxymethyl)imidazolidine 2,5-dione and 4-(3'-anisyl)-4-(carboxymethyl)imidazolidine 2,5-dione, and following the precedures of Example 6A-B, 1',2'-dihydrospiro[imidazolidine-4,4'(3'H)-quinoline]2,2',5-trione,1',2'-dihydrospiro[imidazolidine-4,4'(3'H)-quinoline]2,2',5-trione and 1',2'-dihydrospiro[imidazolidine-4,4'(3'H)-quinoline]2,2',5-trione are prepared, respectively.

EXAMPLE 7

1',2'-dihydro-6'-chlorospiro[imidazolidine-4,4'-(3'H)-quinoline]2,2',5-trione

Chlorine gas was bubbled into a slurry of 1.1 g. (0.0048 mole) of 1',2'-dihydrospiro[imidazolidine-4,4'(3'H)-quinoline]2,2', 5-trione in 75 ml. of water for 2.5 hours. The reaction mixture was poured into 100 ml. of a 10% sodium bisulfite solution and heated until all solids were dissolved. The aqueous solution was extracted with ethyl acetate (4×50 ml.) and the combined extracts washed with a 10% sodium bicarbonate solution, water and brine and dried over magnesium sulfate. The solvent was removed in vacuo and the residue crystallized from ethanol, m.p. 300° C.

Anal. Calc'd. for $C_{11}H_8O_3N_3Cl$ : C, 49.7; H, 3.0; N, 15.8. Found: C, 48.7; H, 3.0; N, 15.4.

The NMR spectrum ($D_6$ DMSO) showed absorption at 11.0 (bs, 1H), 10.47 (s, 1H), 8.6 (s, 1H), 7.37 (d, d, 1H, J=8 and 3), 7.13 (d, 1H, J=3), 6.98 (d, 1H, J=8) and 2.7 (AB, q, 2H, J=20 and 12)ppm.

EXAMPLE 8

2-Hydroxy-6-fluorospiro[chroman-4,4'-imidazolidine]2',5'-dione

To a slurry of 640 mg. (0.002 mole) of 6-fluorospiro[chroman-4,4'-imidazolidine]2,2',5'-trione in 40 ml. of toluene at −78° C. was added 852 mg. (0.006 mole) of diisobutylaluminum hydride in hexane, and the reaction mixture allowed to stir at −78° C. for 30 minutes. The reaction was allowed to warm to 0° C. and was stirred for 24 hours. The reaction was recooled to −40° C., 6 ml. of dry tetrahydrofuran was added and the reaction warmed to 0° C. Additional diisobutylaluminum hydride (1.0 ml) was added in 0.2 ml. portions. The reaction mixture was added to 10% hydrochloric acid and the mixture extracted with ethyl acetate. The combined extracts were washed dried and concentrated to dryness. The residue was chromatographed to give 67 mg. of the desired compound, m.p. 247°–251° C. (dec.).

The NMR spectrum ($D_6$ DMSO) showed absorptions due to a pair of diastereomers at 11.05 (bs, 1H), 8.85 and 8.3 (s, 1H), 7.2–7.08 (m, 1H), 6.93–6.80 (m, 2H), 5.79–5.71 and 5.36–5.27 (m, 1H) and 2.38–1.98 (m, 2H).

EXAMPLE 9

Starting with the appropriate reagents and following the procedure of Example 8, the following compounds are prepared:

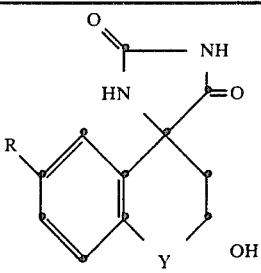

| R    | Y   |
|------|-----|
| F    | CH₂ |
| Cl   | CH₂ |
| H    | CH₂ |
| CH₃  | CH₂ |
| CH₃O | CH₂ |
| H    | O   |
| F    | O   |
| Cl   | O   |
| CH₃  | O   |

I claim:

1. A spiro-imidazolone of the formula

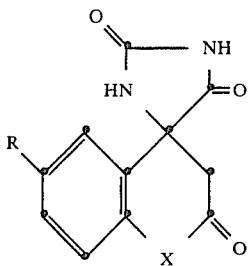

and a pharmaceutically acceptable base salt thereof, wherein R is selected from the group consisting of fluoro, chloro, hydrogen, methyl and methoxy; and X is selected from the group consisting of —O—, $CH_2$ and NH.

2. A compound of claim 1, wherein X is $CH_2$.
3. The compound of claim 2, wherein R is fluoro.
4. The compound of claim 2, wherein R is hydrogen.
5. A compound of claim 1, wherein X is NH.
6. The compound of claim 5, wherein R is chloro.
7. A spiro-imidazolone of the formula

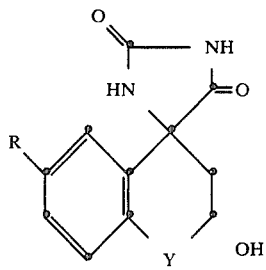

and a pharmaceutically acceptable base salt thereof wherein R is selected from the group consisting of fluoro, chloro, hydrogen, methyl and methoxy; and Y is selected from the group consisting of O and $CH_2$.

8. A compound of claim 7, wherein Y is O.
9. The compound of claim 8, wherein R is fluoro.
10. A pharmaceutical composition which comprises a pharmaceutically-acceptable carrier and a compound selected from claim 1 or claim 7, and wherein the weight-ratio of the pharmaceutically-acceptable carrier to said compound is in the range of 1:4 to 20:1.
11. A method of treating a diabetic host to prevent or alleviate ocular or neuritic diabetes-associated chronic complications, which comprises administering to said diabetic host an alleviating or prophylactically effective amount of a compound selected from claim 1 or claim 7.

* * * * *